United States Patent [19]
Bonte

[11] 4,319,575
[45] Mar. 16, 1982

[54] UNIVERSAL TREPHINE HANDLE

[75] Inventor: Charles A. Bonte, St. Louis, Mo.

[73] Assignee: Storz Instrument Company, St. Louis, Mo.

[21] Appl. No.: 73,214

[22] Filed: Sep. 7, 1979

[51] Int. Cl.$^3$ ............................................. A61B 17/32
[52] U.S. Cl. .................................. 128/305; 128/310; 30/316
[58] Field of Search .............. 128/303 A, 303 R, 326, 128/305, 321, 305.1, 310, 753, 754; 29/235; 30/315, 316, 340, 342, 329, 337; 408/703

[56] References Cited
U.S. PATENT DOCUMENTS

| | | | | |
|---|---|---|---|---|
| 2,473,968 | 6/1949 | Paton | ................................. | 128/305 |
| 3,409,013 | 11/1968 | Berry | ............................... | 128/326 X |
| 4,236,519 | 12/1980 | La Russa et al. | ..................... | 128/305 |

FOREIGN PATENT DOCUMENTS 182855  8/1966  U.S.S.R. ............................... 128/310

OTHER PUBLICATIONS
Martin Motor Trephine Pamphlet (5-1977).

Primary Examiner—Michael H. Thaler

[57] ABSTRACT

A trephine particularly adapted for use in surgical procedures has a universal handle having a tubular portion from which extend a plurality of circumferentially spaced fingers which removably support a tubular trephine blade. In use, the bore of the handle and blade provides a line of sight and illumination along the axis of the trephine to the inside cutting edge of the blade, while additional illumination is allowed to enter through spaces between the fingers. A trephine kit has a universal handle and a variety of different blades for use therewith.

16 Claims, 3 Drawing Figures

UNIVERSAL TREPHINE HANDLE

BACKGROUND OF THE INVENTION

The present invention is directed to a trephine particularly adapted for use in surgical operations such as corneal transplant procedures. More particularly, the present invention relates to a trephine comprising a universal trephine handle adapted to securely and accurately hold different sizes of trephine blades and having a structure which facilitates illumination of the cutting edge and accurate positioning and manipulation thereof.

Trephines are used, for example, in ophthalmic surgery for corneal transplant operations and are employed in various sizes or blade diameters. In corneal transplant procedures the trephine must be precisely positioned and manipulated under a microscope by the surgeon. It is thus of great important that the cutting edge of the blade be well illuminated and that the surgeon have a clear line of sight.

Wherefore, it is an object of the present invention to provide a trephine having a clear line of sight along the axis thereof, so that the trephine can be accurately employed under a microscope by a surgeon without leaving the eyepiece of the microscope. Another object of the present invention is to provide a trephine which facilitates illumination of the inside cutting edge of the trephine blade to allow accurate positioning thereof. Yet another object of the present invention is to provide a trephine having a universal handle upon which different diameter trephine blades can be accurately mounted in alignment with respect to the handle. Still another object of the present invention is to provide a trephine which has minimal light reflection and is easily manipulated by the surgeon. These and other objects, features, and advantages will be apparent from the following description and appended claims, taken in conjunction with the accompanying drawings.

DESCRIPTION OF THE INVENTION

Now referring to the figures, a trephine of the present invention is shown and generally indicated by the numeral 1. Broadly, trephine 1 comprises a universal handle 2 upon which is mounted trephine blade 4. As set forth in detail in the following disclosure, trephine blade 4 is selectively removably mounted on handle 2 and it is contemplated that trephine blades of different diameters will be provided for use with a universal handle.

Figure 1:
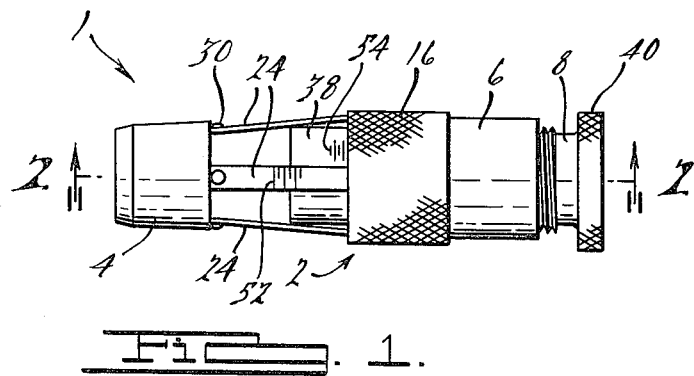
FIG. 1 is a side elevation of a trephine of the present invention.
Figure 2:
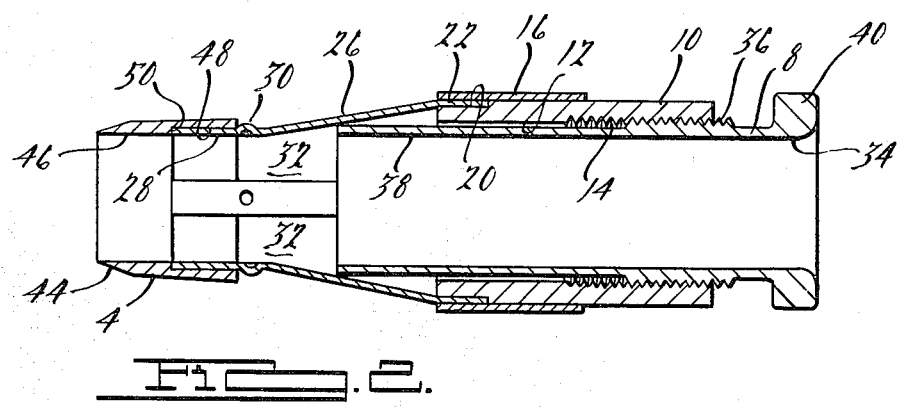
FIG. 2 is a sectional view taken along lines 2—2 of FIG. 1.
Figure 3:
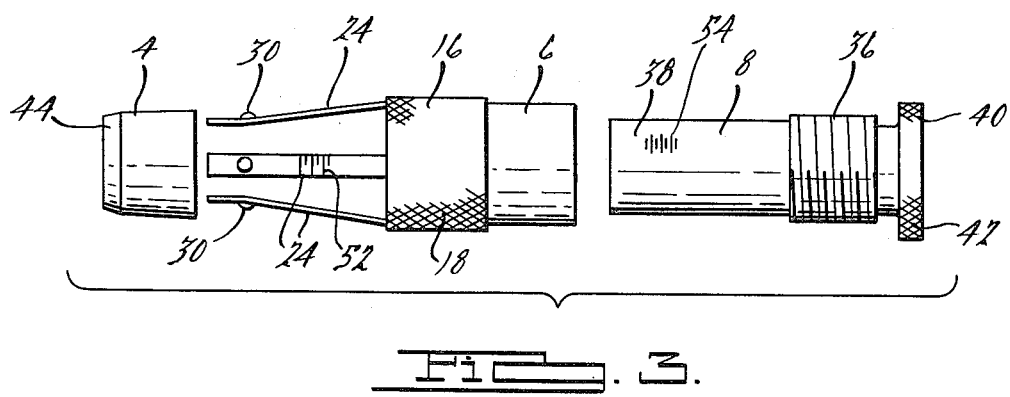
FIG. 3 is an exploded view illustrating the relationship of the separable members of the present invention.

Universal handle 2 has a generally cylindrical shape and comprises two separable members, body 6 and cylindrical barrel 8. Body 6 has a tubular cylinder 10 which has a smooth interior bore 12 at the forward portion thereof and a threaded interior bore 14 at the rearward portion thereof. As used herein "forward" refers to the left as viewed in the figures and "rearward" refers to the right as viewed in the figures. Press fit or otherwise fixedly attached to the forward end portion of cylinder 10 is ring 16 which has a knurled radially outer surface 18 to facilitate manipulation of ring 16, and hence, trephine 1. The forward end portion of cylinder 10 has a plurality of circumferentially spaced axially aligned slots 20 which are located in the radially outward surface portion of cylinder 10. Each slot 20 is sized to receive a rearward end portion 22 of a finger 24. As best shown in FIG. 2, each rearward end portion 22 of each finger 24 is clampingly retained in slot 20 by ring 16. Each finger 24 extends forwardly from cylinder 10 and has an intermediate portion 26 canted slightly from the longitudinal axis of trephine 1. Thus, the forward end portion 28 of each finger 24 is located radially inwardly with respect to the rearward end portion 22 with each forward end portion 28 and rearward end portion 22 extending generally parallel to the longitudinal axis of trephine 1. Each forward end portion 28 has a projection 30 which provides means for stopping rearward movement of blade 4. Fingers 24 are of relatively narrow width and are circumferentially spaced so as to provide open spaces 32 therebetween to allow entry of light to the hollow interior portion of trephine 1 and, hence, illuminate the inside cutting edge of blade 4.

Cylindrical barrel 8 has a smooth interior bore 34.

The radially outer surface of the longitudinally intermediate portion of barrel 8 carries threads 36 which are adapted to threadably engage threaded interior bore 14 of tubular cylinder 10. The unthreaded, forward portion 38 of barrel 8 is of reduced diameter to allow free extension through tubular cylinder 10 while the rearward end portion 40 is of enlarged diameter and has a knurled outer surface 42 to facilitate hand rotation thereof with respect to tubular cylinder 10.

Trephine blade 4 is also tubular in shape and has a cutting edge 44 and an interior bore 46. Bore 46 has an increased diameter portion 48 and a rearward facing shoulder 50 against which abuts the transverse, forward face of each forward end portion 28 of each finger 24. Shoulder 50 provides stop means limiting rearward movement of blade 4 functioning simultaneously with the stop means of projections 30.

A plurality of different trephine blades 4 of different diameters are contemplated for use with the universal handle in accordance with the present invention. For example, trephine blades having diameters of from 6.0 to 9.5 millimeters are suitable. It is contemplated that a kit of a plurality of different size blades and a universal handle will be provided thereby economically providing trephines of various sizes and also facilitating trephine use in the operating room by providing a compact kit of one handle and a plurality of blades which can easily be mounted thereon. Separate trephine blades are, of course, easily sterilized for surgical use.

Further understanding of the present invention will be obtained from the following description of the manipulation of trephine 1. To mount a desired trephine blade 4 onto universal handle 2, the blade 4 is placed coaxial with the forward end portions 28 of fingers 24 with barrel 8 in a rearward position. Fingers 24 are each spring loaded radially inwardly so as to be normally smaller than the inner diameter of the bore 48 of the smallest trephine blade 4. Then barrel 8 is rotated in threaded engagement with tubular cylinder 10 in a direction which urges cylinder 10 forwardly until the forward edge of unthreaded portion 38 comes into abutting relationship with the radially inner surfaces of intermediate portions 26 of each of fingers 24. After a close but slidable fit between fingers 24 and blade 4 is obtained, blade 4 is moved rearwardly to engage the stop means simultaneously provided by shoulder 50 and projections 30. Then, further rotation of barrel 8 causes the forward end portions 28 of fingers 24 to move radially outwardly to clampingly retain trephine blade 4 thereon. Blade size calibrations can be etched on either or both of fingers 24 as at 52 or barrel 8 as at 54 to indicate the proper location of barrel 8 with respect to cylinder 10 for each size trephine blade 4 to facilitate mounting of trephine blades on universal handle 2.

As will be appreciated by those skilled in the art, trephine 1 has a longitudinal bore providing a line of sight for a surgeon along the longitudinal axis thereof to the inside cutting edge of the trephine blade 4. Hence, in use, a surgeon does not have to remove his eye from the eyepiece of a microscope to position and use trephine 1, and microscope light passes through the longitudinal center of trephine 1 to provide illumination of the inside cutting edge of blade 4. In addition, trephine 1 has open spaces 32 which admit further light to the interior of trephine 1. Preferably the trephine of the present invention is made of stainless steel or other material suitable for use in a surgical environment and has a satin, nonglare finish for minimal light reflection.

It will also be appreciated that projections 30 and shoulder 50 on the interior bore of the trephine blade 4 provide secure and accurate positioning and alignment of trephine blade 4 on the forwad end portions 28 which provide means for supporting blade 4. Furthermore, the manipulation of trephine 1 is enhanced by knurled portions 18 and 42 to facilitated rotation of the parts of universal handle 2 to remove or mount a trephine blade or to hold, position and rotate trephine 1 in surgery.

Thus, the specific embodiment of the present invention described herein is well calculated to achieve the objects of the present invention. However, it is evident that those skilled in the art, once given the benefit of the foregoing disclosure may make modifications of the specific embodiment described herein without departing from the spirit of the present invention. Such modifications are intended to be within the scope of the present invention which is limited solely by the scope and spirit of the appended claims.

What is claimed is:

1. A universal trephine handle particularly adapted for use in surgical procedures in combination with a tubular trephine blade, said universal trephine handle comprising:
    a body, said body including a tubular portion, a ring member, and a plurality of fingers, one end portion of each of said fingers being positioned in a slot at a circumferentially spaced location on one end of said tubular portion and extending outwardly generally axially and radially inwardly therefrom, an opposite end portion of each of said fingers being radially movable;
    said ring member being coaxially positioned on said tubular portion for retaining said end portions of said fingers in said slots;
    a tubular member, said tubular member having a portion extending through said tubular portion of said body and being axially movable with respect to said body, said tubular member having one end adapted to engage a radially inwardly facing surface of each of said fingers, axial movement of said tubular member toward said opposite end portions of said fingers urging each of said opposite end portions in a radially outward direction;
    means for supporting said trephine blade on said opposite end portions of said fingers; and
    stop means on said opposite end portion of at least one of said fingers for limiting movement of a trephine blade toward said one end portion of said one of said fingers.

2. The universal trephine handle of claim 1 wherein said tubular member and tubular portion are in threaded engagement with each other.

3. The universal trephine handle of claim 1 wherein said means for supporting said trephine blade comprises generally parallel forward end portions of each of said fingers.

4. The universal trephine handle of claim 1 wherein the total circumferential width of the space between said fingers is greater than the total circumferential width of said fingers and further wherein each of said fingers is spring loaded in a radially inward direction.

5. The universal trephine handle of claim 1 wherein said stop means is a raised projection extending radially outwardly from said fingers.

6. The universal trephine handle of claim 1 wherein said tubular member has a series of marks thereon for indication of the location of said tubular member in said tubular portion and for indication of the size of trephine blade.

7. The universal trephine handle of claim 1 wherein one of said fingers has a series of marks thereon for indication of the location of said tubular member in said tubular portion and for indication of the size of trephine blade.

8. A universal trephine handle particularly adapted for use in surgical procedures in combination with a tubular trephine blade, said universal trephine handle comprising:
    a body, said body including a tubular portion, a ring member and a plurality of fingers, one end portion of each of said fingers being positioned in a slot at a circumferentially spaced location on one end of said tubular portion and extending outwardly generally longitudinally therefrom,
    a tubular member, said tubular member having a portion extending through said tubular portion of said body, said portion extending through said tubular portion being adapted to engage each of said fingers in a direction urging each of said fingers in a radially outward direction,
    means for supporting said trephine blade on another end portion of said fingers,
    said means for supporting said trephine blade comprises generally parallel forward end portions of each of said fingers,
    at least one of said fingers having stop means for limiting movement of said trephine blade on said body, and
    said ring member being coaxially positioned on said tubular portion for retaining said end portion of said fingers in said slots.

9. A trephine particularly adapted for use in surgical procedures comprising:
    a tubular trephine blade;
    a body, said body including a tubular portion, a ring member and a plurality of fingers being positioned in a slot at a circumferentially spaced location on one end of said tubular portion and extending outwardly generally axially and radially inwardly therefrom, an opposite end portion of each of said fingers being radially movable, said ring member retaining said end portions in said slots;

a tubular member, said tubular member having a portion extending through said tubular portion of said body and being axially movable with respect to said body, said tubular member having one end adapted to engage a radially inwardly facing surface of each of said fingers, axial movement of said tubular member in a direction toward said opposite end portions of said fingers urging each of said opposite end portions in a radially outward direction;

means for supporting said trephine blade on said opposite end portions of said fingers; and stop means on said opposite end portion of at least one of said fingers for limiting movement of a trephine blade toward said one end portion of said one of said fingers.

10. A trephine particularly adapted for use in surgical procedures comprising:

a tubular trephine blade, a body, said body including a tubular portion, a ring member and a plurality of fingers, one end portion of each of said fingers being positioned in a slot at a circumferentially spaced location on one end of said tubular portion and extending outwardly generally longitudinally therefrom, said ring member retaining said end portions in said slots, a tubular member, said tubular member having a portion extending through said tubular portion of said body, said portion extending through said tubular portion being adapted to engage each of said fingers in a direction urging each of said fingers in a radially outward direction, said tubular member and said tubular portion in threaded engagement with each other, means for supporting said trephine blade on another end portion of said fingers, said means comprising generally parallel forward end portions of each of said fingers, said trephine blade having an inner bore with a shoulder adapted to abut against a transverse face of each of said fingers, and at least one of said fingers having stop means for limiting rearward movement of said trephine blade on said body.

11. A trephine as in claim 10 wherein said tubular member has a plurality of marks thereon, each of said marks adapted to indicate location of said tubular member in said tubular portion for a trephine blade.

12. A trephine as in claim 10 wherein one of said fingers has a plurality of marks thereon, each of said marks adapted to indicate location of said tubular member with respect to said fingers for a trephine blade.

13. A trephine kit comprising a universal handle and a plurality of tubular trephine blades, said universal handle including:

a body including a tubular portion, a ring member and a plurality of fingers, one end of each of said fingers being positioned in slots in circumferentially spaced locations on one end of said tubular portion and extending outwardly generally longitudinally therefrom, said ring member retaining said one end of said fingers in said slots, a tubular member, said tubular member having a portion extending through said tubular portion of said body, said portion extending through said tubular portion being adapted to engage each of said fingers in a direction urging each of said fingers in a radially outward direction, said tubular member and said tubular portion being in threaded engagement with each other, said end portions of each of said fingers being generally parallel for removably supporting one of said trephine blades, and at least one of said fingers having stop means for limiting rearward movement of said trephine blade on said body.

14. A trephine kit as in claim 13 wherein said tubular member has a plurality of marks thereon, each of said marks adapted to indicate location of said tubular member in said tubular portion for a trephine blade of one diameter.

15. A trephine kit as in claim 13 wherein one of said fingers has a plurality of marks thereon, each of said marks adapted to indicate location of said tubular member with respect to said fingers for a trephine blade of one diameter.

16. A trephine kit as in claim 13 wherein said trephine blade has an inner bore with a shoulder adapted to abut against a transverse end face of each of said fingers.

* * * * *